United States Patent
Zhang

(10) Patent No.: US 6,875,890 B1
(45) Date of Patent: Apr. 5, 2005

(54) METHOD OF PRODUCING N, N-DIMETHYL GLYCINE HYDROCHLORIDE

(76) Inventor: Jiashu Zhang, 2704 S. George La., Diamond Bar, CA (US) 91765

( * ) Notice: Subject to any disclaimer, the term of this patent is extended or adjusted under 35 U.S.C. 154(b) by 0 days.

(21) Appl. No.: 10/881,564

(22) Filed: Jun. 29, 2004

(51) Int. Cl.⁷ ............................................ C07C 205/00
(52) U.S. Cl. ...................... 562/553; 562/400; 562/512; 562/575
(58) Field of Search ................................. 562/553, 400, 562/512, 575

(56) References Cited

U.S. PATENT DOCUMENTS 4,968,839 A * 11/1990 Noell .......................... 562/575

* cited by examiner

Primary Examiner—Rita Desai
Assistant Examiner—Hector M. Reyes
(74) Attorney, Agent, or Firm—Raymond Y. Chan; David and Raymond

(57) ABSTRACT

A process for preparing N,N-Dimethyl Glycine Hydrochloride, comprises treating a chloroacetic acid with aqueous dimethylamine, and then dropping by hydrochloric acid to obtain N,N-dimethyl glycine as well as its hydrochloride salt, wherein decompression process is utilized to assure the product purity and active carbon is employed for cost saving aspect.

15 Claims, 1 Drawing Sheet

US 6,875,890 B1

METHOD OF PRODUCING N, N-DIMETHYL GLYCINE HYDROCHLORIDE

BACKGROUND OF THE PRESENT INVENTION

1. Field of Invention

The invention relates to a producing method for the preparation of N,N-Dimethyl Glycine Hydrochloride, more particularly, relates to an improved process for preparing N,N-Dimethyl glycine hydrochloride in a high purity and high yield rate.

2. Description of Related Arts

Dimethyl glycine (DMG) is a modified amino acid that is found any living body. DMG is produced within the cells of the living body from Choline and Betaine and is so classified as an "intermediary metabolite". Other names for DMG include: Calcium pangamate, pangamic acid, and Vitamin B-15. Meanwhile, DMG could be found in food grains such as rice bran, rice polish and whole grains. It is also found in apricot kernels and brewer's yeast.

DMG plays a crucial role in the respiratory cycle of the cells, transporting oxygen and serving as a potent methyl donor. So far, DMG has been used as an antioxidant, anti-aging, anti-cancer agent and to reduce cholesterol showing a number of beneficial effects. A study in animals showed that immune response to the flu virus and to salmonella was increased from 300% to 1000%. And DMG is a powerful immune booster. DMG enhances both cellular and humoral immunity. DMG has been increase in stamina. In one study, athletes experienced a 40% increase in stamina. DMG helps transport oxygen into cells, increasing their efficiency and preventing lactic acid build-up. It is also effective in autism. In one study 80% of children and adults experienced improvement in their condition. Other studies have shown similar results. Silent children may begin to talk. Results will usually show up within a week though it may range from one day to several weeks. Similarly, in some children with Attention Deficit Disorder (ADD), DMG has improved behavior, speech and frustration threshold within 24 hours. Anecdotally, DMG may reduce the number of seizures in elieptics.

Conclusively, as a nutritional supplement, Dimethyl glycine can improve physical and mental performance by helping the body adapt to the various forms of stress. Athletes could use DMG to improve stamina, reduce muscle cramping and enhance recovery from intense workouts. In short, DMG functions in the body as an indirect methyl donor and serves as a source of 2-carbon species, and serves as mineral transporter-chelating agent. The Nutritional and Physiological properties of DMG come from it being an Ergogenic (tending to increase work output) substance, an anti-stress nutrient, a cell antioxidant, and an immune response potentiator.

Commonly, the conventional producing method to prepare N,N-Dimethyl glycine includes utilizing a monochloro acetic acid to be treated with aqueous dimethyl amine, and then followed by hydrochloric acid to obtain N,N-dimethyl glycine as well as its hydrochloride salt. And the N,N-dimethyl glycine hydrochloride salt should be converted to its free base form through the use of ion exchange resin.

However, the quality and purity of this producing method is not satisfied. Furthermore, the ion exchange resin is very expensive and frequently replacement is costly and inevitable. As a result, an improved producing method for preparing the N,N-dimethyl glycine is highly marketable.

SUMMARY OF THE PRESENT INVENTION

A main object of the present invention is to provide a producing method for preparing N,N-Dimethyl Glycine Hydrochloride in a high purity and yield rate.

Another object of the present invention is to provide a producing method for preparing N,N-Dimethyl Glycine Hydrochloride in a high purity and yield rate, wherein no expensive equipment and raw materials is required.

Another object of the present invention is to provide a producing method for preparing N,N-Dimethyl Glycine Hydrochloride in a high purity and yield rate, wherein no expensive ion exchange resin is needed for yielding final products.

Another object of the present invention is to provide a producing method for preparing N,N-Dimethyl Glycine Hydrochloride in high purity and yield rate, where the final product according to the producing method has same property as traditional producing method.

Accordingly, to achieve the above mentioned objects, the present invention provides a producing process for preparing N,N-Dimethyl Glycine Hydrochloride, said process comprises the steps:

a. adding water to chloroacetic acid to form a solution A;

b. stirringly dropping liquid dimethylamine to the solution A to form a solution B;

c. stirring the solution B, and then, heating the solution B to a predetermined degree and keeping a predetermined period of time to obtain a heated solution B;

d. decompressing and heating the heated solution B to eliminate an ammonia and water to form a decompressed solution B;

e. dropping hydrochloric acid to the decompressed solution B to form a solution C;

f. centrifuging the solution C to obtain a semifinished product;

g. adding deionized water to said semifinished product and heating the deionized semifinished product;

h. adding active carbon to the semifinished product to obtain a filtered solution D;

i. Cooling and centrifuging the filtered solution D to obtain the fine product.

These and other objectives, features, and advantages of the present invention will become apparent from the following detailed description, the accompanying drawings, and the appended claims.

DETAILED DESCRIPTION OF THE PREFERRED EMBODIMENT

Figure 1:
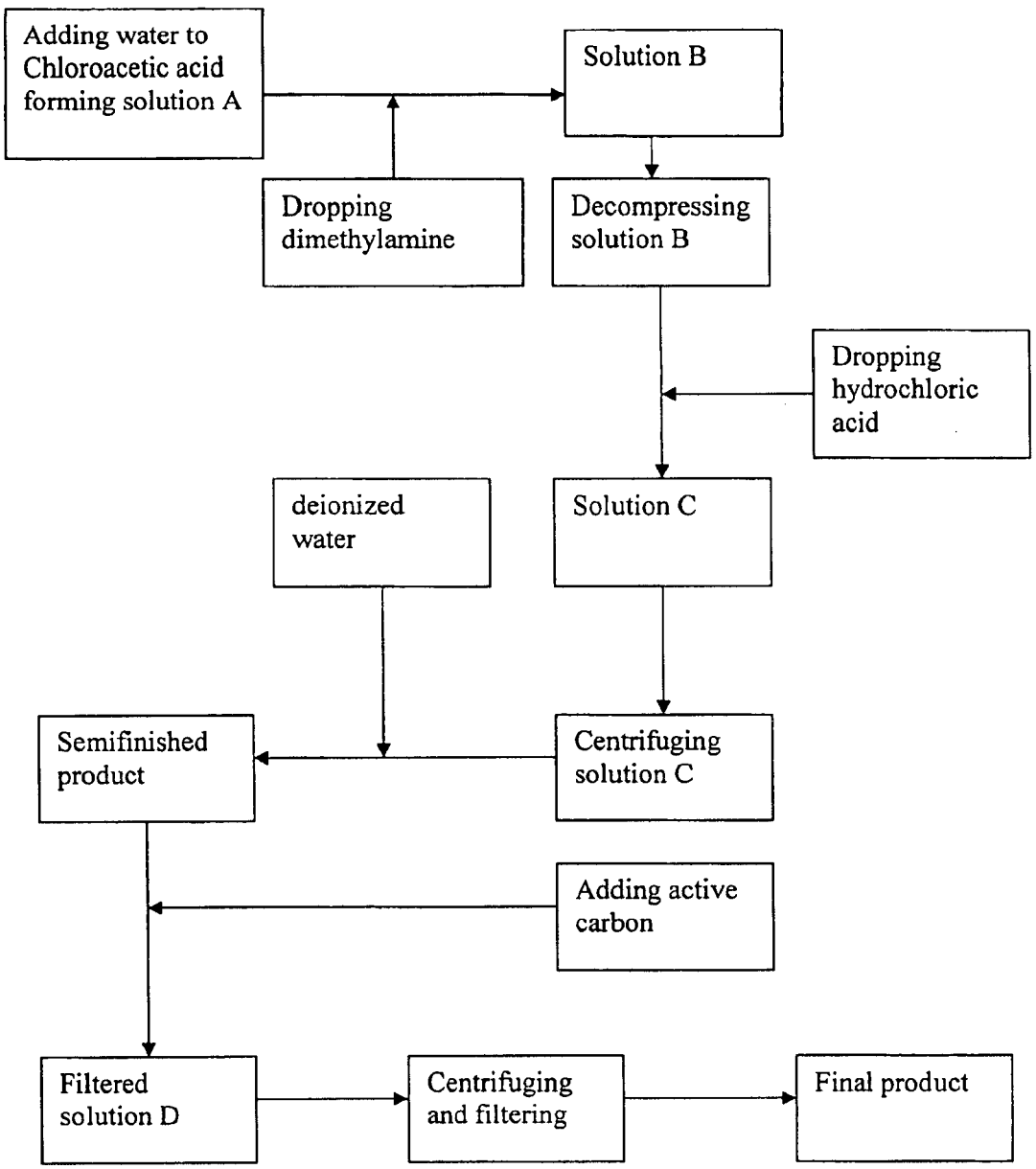
FIG. 1 is a block diagram showing the producing method for preparing N,N-Dimethyl glycine hydrochloride according to the first preferred embodiment of the present invention.

Referring to the FIG. 1, the producing method of N,N-Dimethyl Glycine Hydrochloride according to the first preferred embodiment of the present invention is illustrated. The producing method for preparing N,N-Dimethyl Glycine Hydrochloride comprises the following steps:

a. adding water to chloroacetic acid to form a solution A;

b. stirringly dropping liquid dimethylamine to the solution A to form a solution B;

c. stirring the solution B, and then, heating the solution B to a predetermined degree and keeping a predetermined period of time to obtain a heated solution B;

d. decompressing and heating the heated solution B to eliminate the ammonia and water to form a decompressed solution B;

e. dropping hydrochloric acid to the decompressed solution B to form a solution C;

f. centrifuging the solution C to obtain semifinished product;

g. adding deionized water to said semifinished product and heating the deionized semifinished product;

h. adding a predetermined amount of active carbon to said semifinished product to obtain a filtered solution D;

i. Cooling and centrifuging said filtered solution D to obtain the fine product.

According to the present invention, in the step a, 100 kg of chloroacetic acid are added to 63 kg of water for forming the solution A.

In the step b, the solution A is dropped to 600 liters of liquid dimethylamine to form solution B.

In the step c, the solution B is stirred at a temperature less than 25 degree C., afterwards, the stirred solution B is kept at a temperature less than 30 degree C. for the dropping process, and keep stirring for at least 1 hour, finally, the solution is heated to 50–55 degree C. and kept 10 hours.

In the step d, the solution obtained from the step c is decompressed and heated for eliminating ammonia and water, while the decompression process is stopped at 90 degree C. to make sure the pH Value of the solution is in a range within 6.5–7.0;

In the step e, 158 liters of hydrochloric acid are dropped to the solution formed from step d) at a temperature less than 40 degree C. to form a solution C, afterwards, the solution C is further decompressed to eliminated water, while the decompression process is stopped at 98–100 degree C., finally, the decompressed solution C is collected for testing concentration.

In the step f, the decompressed solution C is centrifugalized at a temperature less than 30 degree C. to obtain a semifinished product, and after the semifinished product is weighted, the parent liquid is concentrated again.

In the step g, 130–160 kg of the semifinished product from step f are added to the same weight of deionized water and heated till dissolved completely to form solution D.

In the step h, active carbon (6% of semofinished product weight) is added to the solution D to form a mixture, and then, the mixture is stirred and keep temperature for half hour, afterwards, the mixture is filtered.

In the step i, the filtrate is cooled and centrifugalized at a temperature below 30 degree C. to obtain the fine product of N,N-Dimethyl Glycine hydrochloride, finally, the parent liquid is concentrated and crystallized continually.

Property of the N,N-Dimethyl Glycine Hydrochloride Made by the Above Producing Method According to the First Preferred Embodiment of the Present Invention.

| | |
|---|---|
| MOLECULAR FORMULA | C4H10NO2CL |
| MOLECULAR WEIGHT | 139.58 |
| APPEARANCE | White crystals |
| MELT POINT | 188–198 degree C. |
| WATER CONTENT | <2% |
| RESIDUE ON IGNITION | <1% |
| HCl CONTENT | 25.5–27.0% |
| DMG CONTENT | 98.0–102.0% |

In view of the fine product of N,N-Dimethyl Glycine Hydrochloride, the appearance is white crystals shaped.

Furthermore, a series of property test is subsequently followed to test the fine product of N,N-Dimethyl Glycine hydrochloride. As shown in above table, the N,N-Dimethyl Glycine Hydrochloride prepared by the producing method according to the first preferred embodiment of the present invention has a distinguished property. In other words, the final product of N,N-Dimethyl Glycine Hydrochloride has a fine purity and lower producing cost.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure form such principles. Therefore, this invention includes all modifications encompassed within the spirit and scope of the following claims.

What is claimed is:

1. A process for preparing N,N-dimethyl Glycine Hydrochloride, comprising the steps of:

(a) adding water to chloroacetic acid to form a solution A;

(b) stirringly dropping a liquid dimethylamine to said solution A to form a solution B;

(c) decompressing and heating said solution B to form a decompressed solution B for eliminating ammonia and water;

(d) adding hydrochloric acid to said decompressed solution B to form a solution C;

(e) centrifuging said solution C to obtain a semifinished product;

(f) adding deionized water to said semifinished product and then heating said semifinished product to form a deionized product;

(g) adding a predetermined amount active carbon to said deionized product, and then filtering said deionized product to obtain a filtered solution D; and (h) cooling and centrifuging said filtered solution D to obtain said N,N-dimethyl Glycine Hydrochloride.

2. The process, as recited in claim 1, wherein the step (b) further comprises the steps of:

(b-1) keeping a temperature less than 30 degree C. during a dropping process for dropping said liquid demethylamine to said solution A;

(b-2) continuously stirring for at least 1 hour during said dropping process;

(b-3) heating said solution B to a temperature range from 50–55 degree C.; and (b-4) keeping said solution B at least 10 hours.

3. The process, as recited in claim 1, wherein the step (c) further comprises the steps of:

(c-1) terminating heating process at 90 degree C.; and (c-2) checking a pH value of said decompressed solution B to make sure said pH value is within a range from 6.5 to 7.0.

4. The process, as recited in claim 1, wherein the step (c) further comprises the steps of:

(c-1) terminating heating process at 90 degree C.; and (c-2) checking a pH value of said decompressed solution B to make sure said pH value is within a range from 6.5 to 7.0.

5. The process, as recited in claim 3, wherein the step (d) further comprises the steps of:

(d-1) maintaining a temperature less than 40 degree C. during a dropping process for dropping said hydrochloric acid to said decompress solution B to form said solution C;

(d-2) eliminating water by a further decompression;

(d-3) stopping said decompression at a temperature within a range from 98 to 100 degree C.; and (d-4) collecting sample of said solution C for a concentration test.

6. The process, as recited in claim 3, wherein the step (d) further comprises the steps of:

(d-1) maintaining a temperature less than 40 degree C. during a dropping process for dropping said hydrochloric acid to said decompress solution B to form said solution C;

(d-2) eliminating water by a further decompression;

(d-3) stopping said decompression at a temperature within a range from 98 to 100 degree C.; and (d-4) collecting sample of said solution C for a concentration test.

7. The process, as recited in claim 5, wherein the step (e) further comprises steps of:

(e-1) keeping a temperature less than 30 degree C. during said centrifuging process for centrifuging said solution C to obtain said semifinished product; and (e-2) weighting said semifinished product.

8. The process, as recited in claim 6, wherein the step (e) further comprises steps of:

(e-1) keeping a temperature less than 30 degree C. during said centrifuging process for centrifuging said solution C to obtain said semifinished product; and (e-2) weighting said semifinished product.

9. The process, as recited in claim 1, wherein in the step (g) 6% of said semifinished product weight of said active carbon is added into said deionized solution.

10. The process, as recited in claim 3, wherein in the step (g) 6% of said semifinished product weight of said active carbon is added into said deionized solution.

11. The process, as recited in claim 4, wherein in the step (g) 6% of said semifinished product weight of said active carbon is added into said deionized solution.

12. The process, as recited in claim 7, wherein in the step (g) 6% of said semifinished product weight of said active carbon is added into said deionized solution.

13. The process, as recited in claim 8, wherein in the step (g) 6% of said semifinished product weight of said active carbon is added into said deionized solution.

14. The process, as recited in claim 12, wherein the step (h) further comprises the steps of:

(h-1) keeping a temperature less than 30 degree C. during said cooling and centrifuging process for centrifuging said filtered solution D to obtain a fine product of said N,N-dimethyl Glycine Hydrochloride; and (h-2) Obtaining said N,N-dimethyl Glycine Hydrochloride.

15. The process, as recited in claim 13, wherein the step (h) further comprises the steps of:

(h-1) keeping a temperature less than 30 degree C. during said cooling and centrifuging process for centrifuging said filtered solution D to obtain a fine product of said N,N-dimethyl Glycine Hydrochloride; and (h-2) Obtaining said N,N-dimethyl Glycine Hydrochloride.

* * * * *